(12) United States Patent
Maestri et al.

(10) Patent No.: US 9,725,578 B2
(45) Date of Patent: Aug. 8, 2017

(54) STERICALLY HINDERED POLYMERIC AMINES AND THEIR USE AS POLYMER STABILIZERS

(75) Inventors: Francesco Maestri, Bergamo (IT); Simone Del Sordo, Treviglio (IT); Ferruccio Berte, Bergamo (IT)

(73) Assignee: 3V SIGMA S.P.A., Milan (MI) (IT)

( * ) Notice: Subject to any disclaimer, the term of this patent is extended or adjusted under 35 U.S.C. 154(b) by 27 days.

(21) Appl. No.: 13/879,973

(22) PCT Filed: Oct. 27, 2011

(86) PCT No.: PCT/EP2011/068867
§ 371 (c)(1),
(2), (4) Date: Apr. 19, 2013

(87) PCT Pub. No.: WO2012/055965
PCT Pub. Date: May 3, 2012

(65) Prior Publication Data
US 2013/0203904 A1    Aug. 8, 2013

(30) Foreign Application Priority Data

Oct. 28, 2010 (IT) .............................. MI2010A2006

(51) Int. Cl.
*C07D 413/00* (2006.01)
*C08K 5/34* (2006.01)
(Continued)

(52) U.S. Cl.
CPC .......... *C08K 5/3492* (2013.01); *C07D 401/14* (2013.01); *C07D 413/14* (2013.01); *C08K 5/34926* (2013.01); *C09K 15/30* (2013.01)

(58) Field of Classification Search
CPC  C08K 5/3492; C08K 5/34926; C07D 401/14; C07D 413/14; C09K 15/30
(Continued)

(56) References Cited

U.S. PATENT DOCUMENTS 4,086,204 A    4/1978  Cassandrini et al.
4,331,586 A    5/1982  Hardy
(Continued)

FOREIGN PATENT DOCUMENTS

| EP | 1 780 237 A2 | 10/2006 |
|----|---|---|
| EP | 2 112 198 A1 | 3/2009 |
| EP | 2 216 364 A1 | 2/2010 |

OTHER PUBLICATIONS

Grzegorz Blotny, Recent applications of 2,4,6-trichloro-1,3,5-triazine and its derivatives in organic synthesis, Tetrahedron 62 (2006) 9507-9522.*

(Continued)

*Primary Examiner* — Susannah Chung
*Assistant Examiner* — Robert T Butcher
(74) *Attorney, Agent, or Firm* — Silvia Salvadori, P.C.; Silvia Salvadori

(57) ABSTRACT

The present invention relates to polypiperidine compounds of polymeric type which are capable of conferring to the polymeric materials, particularly to polyolefins, a high stability against photodegradation and oxidative action of air, belong to the HALS category and have general formula (I):

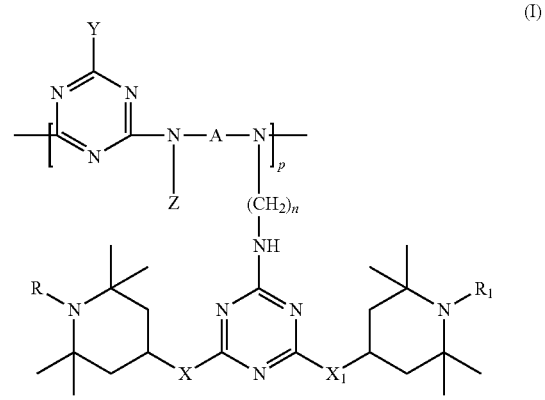

wherein p is from 3 to 20;

n is from 2 to 12;

R and $R_1$, which are the same or different, are selected in the group consisting of hydrogen, linear and branched $C_1$-$C_{12}$ alkyl groups, alkenyl groups having 3 to 8 carbon atoms and aralkyl groups having 7 to 19 carbon atoms;

X and $X_1$, which are the same or different, are selected in the group consisting oxygen and groups of formula (II)

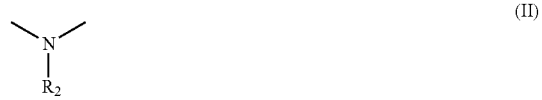

wherein $R_2$ is selected in the group consisting of hydrogen, linear and branched $C_1$-$C_{12}$ alkyl groups, cycloalkyl groups having 5 to 12 carbon atoms and aralkyl groups having 7 to 12 carbon atoms;

A represents a —$(CH_2)_a$— group wherein a is from 2 to 12, with the proviso that a is different from n;

(Continued)

Z is selected in the group consisting of $C_1$-$C_{18}$ alkyl groups, groups of formula (III)

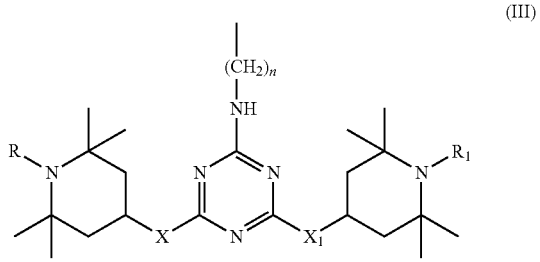

(III)

wherein n, X, $X_1$, R and $R_1$ are as above defined, and groups of formula (IV)

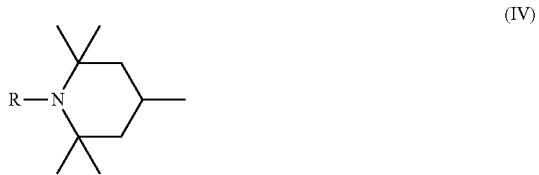

(IV)

wherein R is as above defined;
Y represents a substituent selected in the group consisting of the groups of general formula (V)

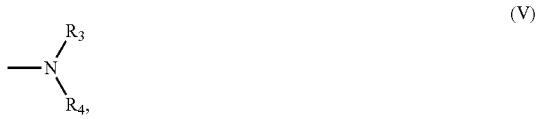

(V)

the groups O—$R_4$ and S—$R_4$,
wherein $R_3$ and $R_4$, which may be the same or different, represent hydrogen, a linear and branched $C_1$-$C_{18}$ alkyl group, a cycloakyl group having 5 to 12 carbon atoms, an aralkyl group having 7 to 12 carbon atoms, an aryl group having 6 to 12 carbon atoms or may form, together with the nitrogen atom to which they are linked, a heterocycle containing 5 to 7 carbon atoms;
and the piperidine group (VI)

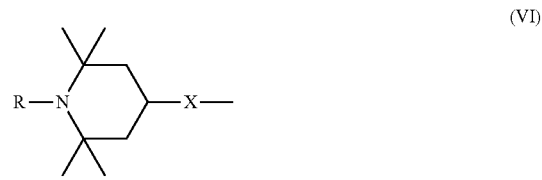

(VI)

wherein R and X are as above defined.
The invention further relates to the processes for preparation of the compounds according to the invention.

13 Claims, 2 Drawing Sheets

(51) Int. Cl.
    *C08K 5/3492*     (2006.01)
    *C07D 403/00*    (2006.01)
    *C07D 401/14*    (2006.01)
    *C09K 15/30*     (2006.01)
    *C07D 413/14*    (2006.01)
(58) Field of Classification Search
    USPC .................................. 524/100; 544/113, 212
    See application file for complete search history.

(56)          References Cited

U.S. PATENT DOCUMENTS 4,477,615 A  * 10/1984 Raspanti et al. .............. 524/100
    2009/0270535 A1* 10/2009 Berte .................. C08K 5/3435
                                                           524/100
    2009/0270536 A1* 10/2009 Berte' .................. C07D 251/70
                                                           524/100

OTHER PUBLICATIONS

International Search Report dated Dec. 6, 2011 of International Application No. PCT/EP2011/068867 and Written Opinion.

* cited by examiner

HALS 1

HALS 2

HALS 3

HALS 4

STERICALLY HINDERED POLYMERIC AMINES AND THEIR USE AS POLYMER STABILIZERS

CROSS-REFERENCE TO RELATED APPLICATION

This application is a 371 of PCT/EP2011/068867, filed Oct. 27, 2011, which in turn claims the benefit of priority from Italian Patent Application Serial No. MI2010A002006, filed Oct. 28, 2010, the contents of each of which are incorporated herein by reference.

Field of the Invention

The present invention relates to novel polypiperidine compounds, of polymeric type, which are able to impart to synthetic polymeric materials, in particular to polyolefins, a high stability towards photodegradation and air oxidation. The invention further relates to processes for the preparation of the compounds according to the invention.

Background of the Invention

It is known that synthetic polymeric materials are subject to deterioration due to the action of heat, sun light and air, which can cause degradation, loss of mechanical properties, discoloring and other undesired effects.

Various classes of compounds have been proposed for the stabilization of polymeric materials, principally against UV radiation of the solar light, some of which had a wide range of applicability, such as for example benzophenones and benzotriazoles. These compounds confer to the polymers an acceptable stability, which is however not yet sufficient for the practical needs with reference to the fibers, films and raffia made of olefinic polymers.

Polyalkylpiperidine derivatives, normally denominated HALS (Hindered Amine Light Stabilizers) are very effective for the stabilization of polymeric materials. A number of patents describe their preparation, use and the obtained results, such as for example U.S. Pat. No. 4,477,615, U.S. Pat. No. 4,331,586, U.S. Pat. No. 4,086,204.

However, not always do said known stabilizers give satisfying results and the polymeric materials remain subject to undesired deterioration due to heat, light and air, with the above mentioned negative consequences. One of the reasons for this deterioration is diffusion and migration of the polypiperidine stabilizers inside the polymeric material whose stability towards oxidative action and photodegradation has to be improved. A reduced migration of the polypiperidine derivatives may therefore be a factor for increasing stability of synthetic polymeric material towards oxidative action and photodegradation caused by heat, light and air. A further drawback of the stabilizer compounds according to the prior art is that their synthesis requires the use of industrially expensive working conditions.

SUMMARY OF THE INVENTION

Object of the present invention is providing new high molecular weight polypiperidine compounds of polymeric type which are able to confer to the synthetic polymeric materials the above mentioned improved stability features. Said object is obtained with the polymeric polypiperidine compounds whose main features are specified in claim 1, and with a process for the fabrication thereof, whose main features are specified in claim 8. Other features of the invention are specified in the remaining claims.

BRIEF DESCRIPTION OF THE DRAWINGS

Further advantages and features of the compounds according to the present invention will be clear to the skilled persons from the following detailed and non-limiting description of some embodiments thereof, with reference to the attached drawings wherein.

DETAILED DESCRIPTION OF THE INVENTION

Figure 1:
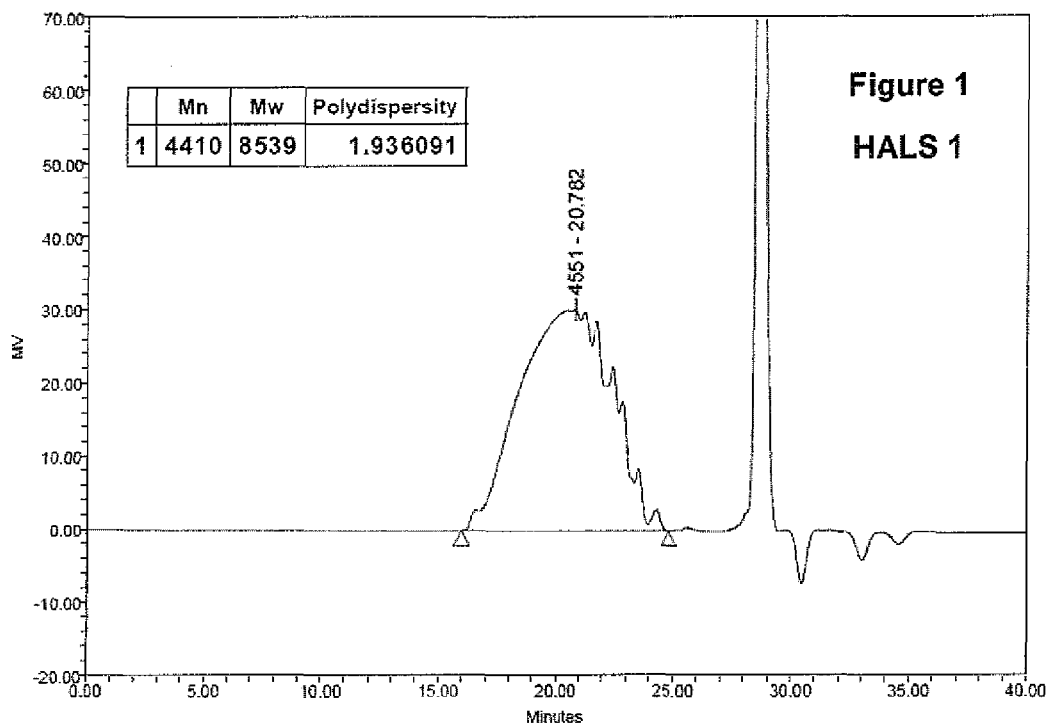
FIG. 1 shows a chromatogram referring to a high molecular weight polymeric polypiperidine compound according to the invention, obtained as described in the following example 1.

According to the present invention, it is possible to confer to the synthetic polymeric materials a particularly high stability towards photodegradation and air oxidative action by using polymeric HALS, which are able to guarantee a reduced migration inside the polymeric materials to be stabilized, having the following general formula (I):

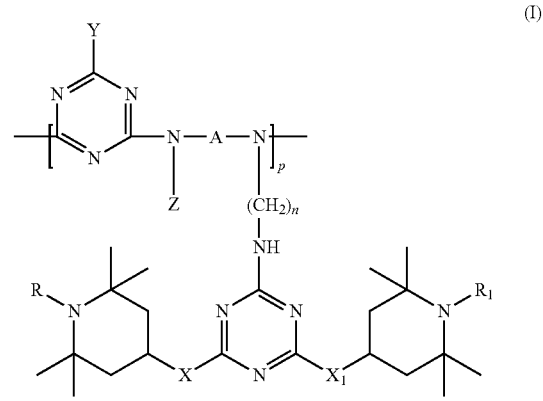

(I)

wherein p is from 3 to 20;

n is from 2 to 12;

R and $R_1$, which are the same or different, are selected in the group consisting of hydrogen, linear and branched $C_1$-$C_{12}$ alkyl groups, alkenyl groups having 3 to 8 carbon atoms and aralkyl groups having 7 to 19 carbon atoms;

X and $X_1$, which are the same or different, are selected in the group consisting of oxygen and groups of formula (II)

(II)

wherein $R_2$ is selected in the group consisting of hydrogen, linear and branched $C_1$-$C_{12}$ alkyl groups, cycloalkyl groups having 5 to 12 carbon atoms and aralkyl groups having 7 to 12 carbon atoms;

A represents a —$(CH_2)_a$— group wherein a is from 2 to 12, with the proviso that a is different from n;

Z is selected in the group consisting of $C_1$-$C_{18}$ alkyl groups, groups of formula (III)

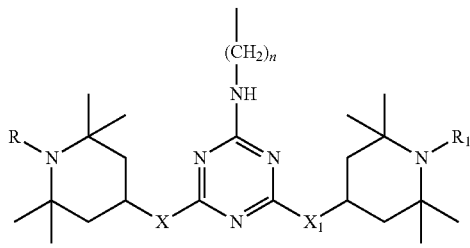
(III)

wherein n, X, $X_1$, R and $R_1$ are as above defined, and groups of formula (IV)

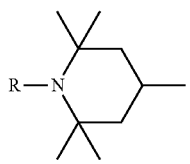
(IV)

wherein R is as above defined;

Y represents a substituent selected in the group consisting of the groups of general formula (V)

(V)

the groups O—$R_4$ and S—$R_4$, wherein $R_3$ and $R_4$, which may be the same or different, are selected in the group consisting of hydrogen, linear and branched $C_1$-$C_{18}$ alkyl groups, cycloalkyl groups having 5 to 12 carbon atoms, aralkyl groups having 7 to 12 carbon atoms, aryl groups having 6 to 12 carbon atoms, or may form, together with the nitrogen atom to which they are linked, a heterocycle containing 5 to 7 carbon atoms;

and the piperidine group (VI)

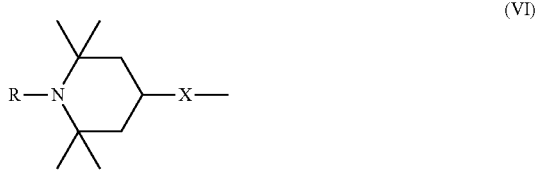
(VI)

wherein R and X are as above defined.

It has been found and it is claimed by the present inventors that the polypiperidine derivatives of formula (I), wherein p is included between 3 and 20, are capable of conferring an improved stability to the synthetic polymeric materials towards oxidative action and photodegradation. As a matter of fact, the reduced diffusion inside the synthetic polymeric material of the novel polymeric HALS of formula (I) (according to the REACH legislation) guarantees a lower degradation due to exposure to sun light and heat. Further, the process according to the present invention for the preparation thereof is simple and industrially not very expensive.

Preferably, the polypiperidine derivatives according to the present invention belong to the general formula (I) wherein p is from 3 to 8, and more preferably from 3 to 6.

It has been noted that the polypiperidine derivatives of polymeric type according to formula (I), in particular with n=3 and A=—$(CH_2)_a$— with a=2 confer to the polymeric materials a better stability against photodegradation and the oxidative action of air.

Further, it has been found that the stability is also improved when the group Z corresponds to the group of formula (III), where R and $R_1$ are the same and particularly hydrogen or methyl and when X and $X_1$, equal to each other, are groups of formula (II) wherein particularly $R_2$ is a butyl group.

Further improvements in the stability conferred to the polymeric materials are observed when Y is the group of formula (VI) or a morpholine group.

The polypiperidine compounds of formula (I) wherein Y is a morpholine group advantageously show a particularly good performance in the stabilization of polyamides (PA) and of the acrylonitrile-butadiene-styrene copolymers (ABS).

The present invention also relates to the processes for the preparation of polymeric polypiperdine compounds of formula (I).

Obtaining the polymeric polypiperidine compounds of formula (I) is possible, according to the present invention, through a polycondensation reaction between an intermediate of general formula (VII)

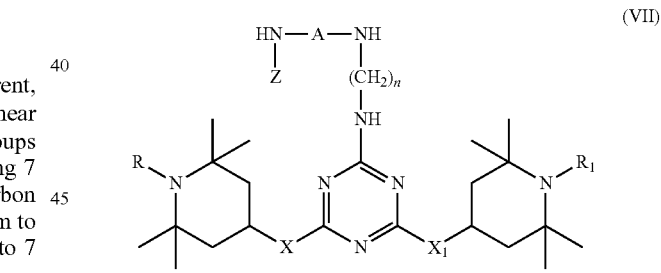
(VII)

wherein Z, A, R, $R_1$, X, $X_1$ and a are as above defined, and cyanuric chloride.

When Z is a $C_1$-$C_{18}$ alkyl group, the group of formula (VII) can be obtained through a process consisting in reacting an amine having the following general formula (VIII)

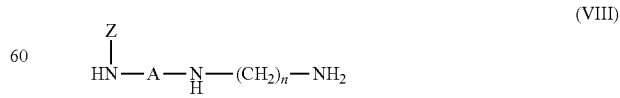
(VIII)

wherein Z, A and a are as above defined, with an equivalent of the derivative having the following general formula (IX) whose preparation is well known in the literature (for example, Example 3 of WO2007/057265A2)

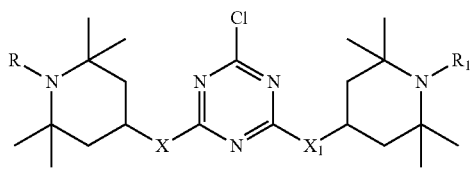

(IX)

wherein R, R$_1$, X and X$_1$ are as above defined.

Thus, a derivative is obtained that can be represented through the following simplified formula (VII):

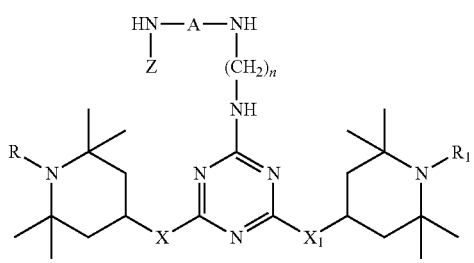

(VII)

wherein Z=C$_1$-C$_{18}$ and A, R, R$_1$, X, X$_1$ and n are as above defined.

Alternatively, the derivative of general formula (IX)

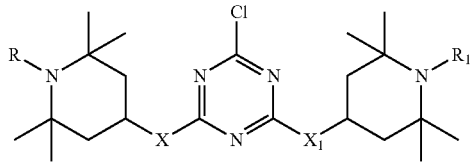

(IX)

wherein R, R$_1$, X and X$_1$ are as above defined is reacted in equimolar quantities with a generic diamine of formula (X)

NH$_2$—(CH$_2$)$_n$—NH$_2$ (X)

wherein n is as above defined,
a derivative of formula (XI) is obtained, whose preparation is also described in Example 1 of U.S. Pat. No. 4,322,337,

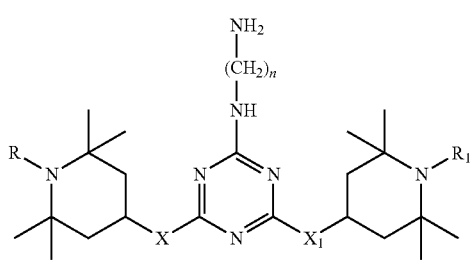

(XI)

wherein R, R$_1$, X, X$_1$ and n are as above defined.

By reaction of two equivalent moles of the derivative of general formula (XI) with a group of formula (XII)

B-A-B (XII)

wherein A is as above defined and B represents a halogen selected between chlorine and bromine
the derivative of general formula (VII) can be obtained

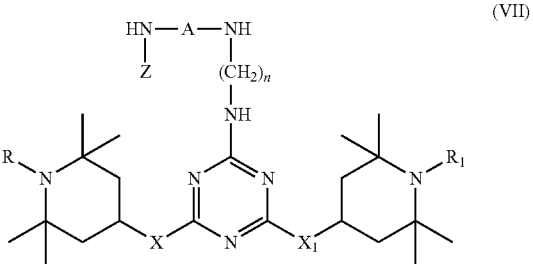

(VII)

wherein Z=formula (III) group and A, R, R$_1$, X, X$_1$ and n are as above defined. As a further alternative, by reacting an amine of general formula (XIII)

H$_2$N—(CH$_2$)$_n$—N(H)—A—N(H)—(CH$_2$)$_n$—NH$_2$ (XIII)

wherein A and n are as above defined
with the above described derivative having the general formula (IX) a derivative can be obtained represented by simplified formula (VII)

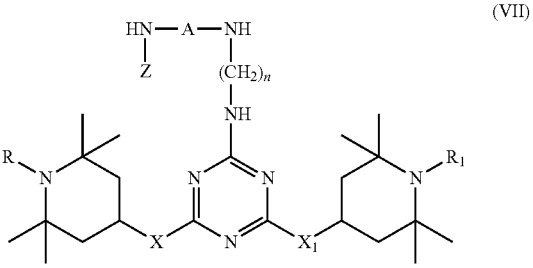

(VII)

wherein Z=group of formula (III) and A, R, R$_1$, X, X$_1$ and n are as above defined.

The synthetic polycondensation step, that involves as reactants the formula (VII) reactant and cyanuric chloride, takes place in an inert aprotic solvent selected among toluene, xilene, mesitylene, tetralin, decalin, acetone, dimethylformamide or other aprotic solvents. Preferably, the reaction is carried out in the presence of an acidity acceptor; highly water soluble inorganic bases are particularly preferable, such as for example alkaline metal hydroxides or carbonates. Sodium hydroxide or potassium hydroxide are normally used, and the reaction is carried out by using water solutions of these inorganic bases at a weight percent concentration of from 20% to 50%, preferably from 25% to 50%. The reaction takes place in a temperature range of from 5° C. and 140° C., preferably from 10° C. and 130° C. and more preferably from 25° C. and 120° C.

The reaction involves the initial mixing of a solution of the compound of formula (VII) with cyanuric chloride (in solution or solid). The mixing is carried out at a temperature of between 5° C. and 60° C., preferably between 20° C. and 35° C. The addition of cyanuric chloride (in solution or solid) to a solution of the compound of formula (VII) as well as the addition of a solution of the compound of formula (VII) to a solution of cyanuric chloride, brings about the formation of a reactive species capable of subsequently initiating the polycondensation process. Anyway, it has been found that the addition of a solution of cyanuric chloride to a solution of the compound of formula (VII) is preferable.

The addition of an acidity corrector, and the progressive heating of the reaction mixture at a temperature of between 80° C. and 120° C., preferably of between 90° C. and 110° C. brings about formation of the polymeric polypiperidine derivative of formula (XIV)

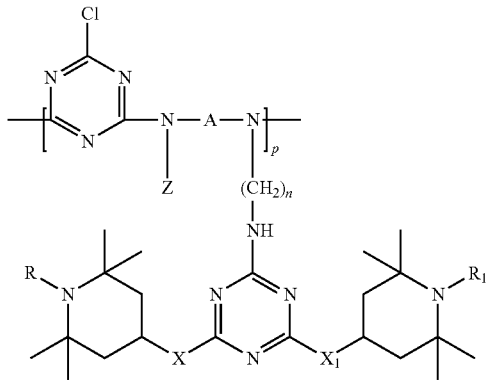

(XIV)

wherein p=3-20 and Z, A, R, $R_1$, X, $X_1$ and n have the above defined meaning.

The use of a light excess of the compound of formula (VII) during the polycondensation step has been found to be advantageous. An excess of between 5 and 25 moles %, and preferably of between 10 and 20 moles % has allowed a polymerization grade p included between 3 and 20, preferably between 3 and 8 and even more preferably between 3 and 6.

By reaction of the polymeric derivative of formula (XIV) with the suitable groups H—Y, wherein Y corresponds to the group of formula (V) or to groups $OR_4$ and $SR_4$, with $R_3$ and $R_4$ being as above defined, new polymeric HALS of formula (I) have been obtained:

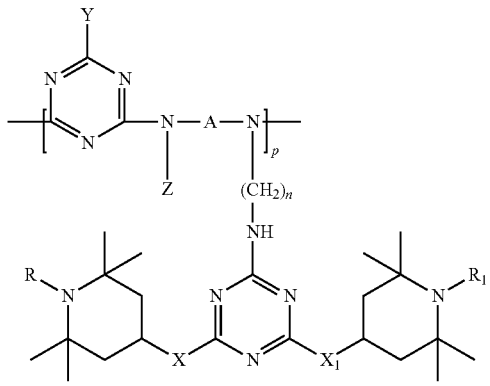

(I)

wherein p, Y, Z, A, X, $X_1$, R, $R_1$ and n have the above defined meanings.

The reaction of the polymeric derivative of formula (XIV) with H—Y, wherein H—Y is morpholine, is particularly simple and economical since it proceeds under mild conditions and provides the desired polypiperidine compound of formula (I) in high yields.

The terminal groups of the HALS of formula (I) can be H, OH, $OR_5$ wherein $R_5$=alkyl or amine group, particularly amine group derived from formula (VII).

The step sequences of the process according to the invention can be used in order to obtain high polycondensation values in other polypiperidine derivatives (HALS) in the repeating unit of which a triazine unit is present.

The quantities of HALS according to the present invention necessary for an efficient stabilization of the polymeric materials depends on different factors, such as the type and the features of the polymeric material to be stabilized, the use for which said material is intended, the intensity of the radiations and the duration of the foreseen exposure to which the material has to be subjected.

In a particular embodiment thereof the present invention consists in adding the compounds of formula (I) to the polymeric material that has to be stabilized in quantities of between 0.01 and 5% by weight with respect to the polymeric material, preferably between 0.1 and 1.0%. Particularly advantageous results are obtained if the polymeric material is a polyolefin.

In further embodiments of the present invention the above mentioned composition comprises, as polyolefin material stabilizers, besides the HALS of formula (I), other monomeric, polymeric or macromolecular HALS of different nature.

The polymers that can be advantageously stabilized according to the present invention are polyethylene, polypropylene, polystyrene, polybutadiene, polyisoprene, and copolymers thereof such as the acrylonitrile-butadiene-styrene copolymer; polyvinylchloride, polyvinylidene chloride and copolymers thereof, polyvinylacetate and copolymers thereof, in particular with ethylene, polyesters such as polyethyleneterephtalate; polyamides, such as for example nylon 6 and nylon 6,6; polyurethans.

The compounds of the present invention can be incorporated into the polymeric materials by any known method for mixing additives and polymeric materials such as by:

mixing with the polymer, which may be in form of powder or granulated in a suitable mixer or extruder;

adding in the form of a solution or suspension in a suitable solvent and subsequently removing the solvent from the polymer, which may be in firm of powder, granulated or in suspension, after thorough mixing;

adding to the polymer during preparation thereof, for example during the last stage of preparation.

The compounds of formula (I) may be added to the polymeric materials to be stabilized together with HALS of different type as above mentioned, as well as antioxidants based on phenols, amines, phosphites; UV radiation sorbers based on benzophenones, benzotriazoles; nickel stabilizers; plasticizers, lubrifiers, antistatic agents, fire retardants, corrosion inhibitors, metal deactivators, mineral fillers such as titanium dioxide, aluminium oxide and similar. Some examples of said additives are the following:

A. Antioxidants

Alkylated phenols, such as 2,6-di-tert-butyl-4-methylphenol; 2-(tert-butyl)-4,6-dimethylphenol; 2,6-di-tert-butyl-4-ethylphenol; 2,6-di-tert-butyl-4-butylphenol; 2,6-di-tert-butyl-4-isobutylphenol; 2,6-di-cyclopentyl-4-methylphenol; 2-(α-methylcyclohexyl)-4,6-dimethylphenol; 2,6-di-octadecyl-4-methylphenol; 2,4,6-tricyclohexylphenol; 2,6-di-tert-butyl-4-(methoxymethyl)phenol; linear or branched nonyl-phenols, such as 2,6-di-cyclononyl-4-methylphenol; 2,4- dimethyl-6-(1'-methylundecyl)phenol; 2,4-dimethyl-6-(1'-heptadecyl)phenol and mixtures thereof.

2. Alkyl-tiomethyl phenols, such as for example 2,4-di-octylthiomethyl-6-tert-butylphenol, 2,4-di-octylthiomethyl-6-methylphenol, 2,4-di-octylthiomethyl-6-ethylphenol, 2,6-di-dodecylthiomethyl-4-nonylphenol.

3. Hydrochinones and alkylated hydrochinones, such as for example: 2,6-di-tert-butyl-4-methoxyphenol; 2,5-di-tert-butyl-hydrochine; 2,5-di-tert-amyl-hydrochinone; 2,6-diphenyl-4-octadeciloxyphenol; 2,6-di-tert-butyl-hydrochinone; 2,5-di-tert-butyl-4-hydroxyanisole; 3,5-di-tert-butyl-4-hydroxyanisole; 3,5-di-ter-butyl-4-hydroxyphenylstearate; bis(3,5-di-tert-butyl-4-hydroxyphenyl)adipate.

4. Tocopherols, for example α-tocopherol; γ-tocopherol; β-tocopherol; δ-tocopherol and mixtures thereof (vitamin E).

5. Hydroxylated thiodiphenyl ethers, such as 2,2'-thiobis(6-tert-butyl-4-methylphenol); 2,2'-thiobis(4-octylphenol); 4,4'-thiobis(6-tert-butyl-3-methylphenol); 4,4'-thiobis(6-tert-butyl-2-methyl-phenol); 4,4'-bis[2,6-dimethyl-4-hydroxyphenyl]disulfide.

6. Alkylidene bisphenols, such as 2,2'-methylene-bis(6-tert-butyl-4-methylphenol); 2,2'-methylene-bis(6-tert-butyl-4-ethylphenol); 2,2'-methylene-bis(4-methyl-6-(α-methylcyclohexyl)phenol); 2,2'-methylene-bis(4-methyl-6-cyclohexylphenol); 2,2'-methylene-bis(6-nonyl-4-methylphenol); 2,2'-methylene-bis-(4,6-di-tert-butylphenol); 2,2'-ethylidene-bis(4,6-di-tert-butylphenol); 2,2'-ethylidene-bis(6-tert-butyl-4-isobutylphenol), 2,2'-methylene-bis(6-(α-methylbenzyl)-4-nonylphenol); 2,2'-methylenebis(6-(α-α-dimehylbenzyl)-4-nonylphenol); 4,4'-methylenebis(2,6-di-tert-butyl-phenol); 4,4'-methylenebis(6-tert-butyl-2-methylphenol); 1,1-bis(5-tert-butyl-4-hydroxy-2-methylphenyl)butane; 2,6-bis(3-tert-butyl-5-methyl-2-hydroxybenzyl)-4-methyphenol; 1,1,3-tris(5-tert-butyl-4-hydroxy-2-methylphenyl)butane; 1,1-bis(5-tert-butyl-4-hydroxy-2-methylphenyl)-3-n-dodecyl-mercaptobutane; ethylene glycol bis-(3,3-bis-(3'-tert-butyl-4'-hydroxyphenyl)-butyrate); bis(2-(3'-tert-butyl-2'-hydroxy-5'-methylbenzyl)-6-tert-butyl-4-methylphenyl)terephtalate; bis(3-tert-butyl-4-hydroxy-5-methylphenyl)dicyclopentadiene; 1,1-bis(3,5-dimethyl-2-hydroxyphenyl)butane; 2,2-bis-(3,5-di-tert-butyl-4-hydroxyphenyl)propane; 2,2-bis-(5-tert-butyl-4-hydroxy-2-methylphenyl)-4-n-dodecyl-mercaptobutane, 1,1,5,5-tetra-(5-ter-butyl-4-hydroxy-2-methylphenyl)pentane.

7. O-, N- and S-benzyl derivates such as: 3,5,3',5'-tetra-ter-butyl-4-4'-dihydroxydibenzyl ether; octadecyl-4-hydroxy-3,5-dimethylbenzyl-mercapto acetate; tridecyl-4-hydroxy-3,5-di-ter-butyl-benzylmercapto acetate; tri(3,5.di-tert-butyl-4-hydroxybenzyl)amine; bis(4-tert-butyl-3-hydroxy-2,6-dimethylbenzyl)dithioterephtalate; bis(3,5-di-tert-butyl-4-hydroxybenzyl)disulphide; isooctyl-3,5-di-tert-butyl-4-hydroxybenzylmercaptoacetate.

8. Malonates containing the hydroxybenzyl groups such as; dioctadecyl-2,-2,2-bis(3,5-di-tert-butyl-2-hydroxybenzyl)malonate; dioctadecyl-2,-(3-tert-butyl-4-hydroxy-5-methylbenzyl)malonate; di-dodecylmercaptoethyl-2,2'-bis-(3,5-di-tert-butyl-4-hydroxybenzyl)malonate; bis-(4-(1,1,3,3-tetramethlbutyl-phenyl)-2,2-bis-(3,5-di-tert-butyl-4-hydroxybenzyl)malonate.

9. Hydroxybenzyl aromatic compounds, such as 1,3,5-tris-(3,5-di-tert-butyl-4-hydroxybenzyl)-2,4,6-trimethylbenzene; 1,4-bis(3,5-di-tert-butyl-4-hydroxybenzyl)-2,3,5,6-tetramethylbenzene; 2,4,6-tris-(3,5-di-tert-butyl-4-hydroxybenzyl)-phenol.

10. Triazine derivates, such as 2,4-bis(octylmercapto)-6-(3,5-di-tert-butyl-4-hydroxyanilino)-1,3,5-triazine; 2-octylmercapto-4,6-bis(3,5-di-tert-butyl-4-hydroxyanilino)-1,3,5-triazine; 2-octylmercapto-4,6-bis(3,5-di-tert-butyl-4-hydroxyphenoxy)-1,3,5-triazine; 2,4,6-tris(3,5-di-tert-butyl-4-hydroxyphenoxy)-1,3,5-triazine; 1,3,5-tris(3,5-di-tert-butyl-4-hydroxybenzyl)-isocyanurate; 1,3,5-tris-(4-tert-butyl-3-hydroxy-2,6-dimethylbenzyl)isocyanurate; 2,4,6-tris(3,5-di-tert-butyl-4-hydroxyphenylethyl)-1,3,5-triazine; 1,3,5-tris-(3,5-di-tert-butyl-4-hydroxyphenylpropionyl) hexahydro-1,3,5-triazine; 1,3,5-tris-(3,5-dicyclohexyl-4-hydroxybenzyl)isocyanurate.

11. Benzylphosphonates, such as for example: dimethyl-2,5-di-tert-buthyl-4-hydroxybenzylphosphonate; diethyl-3,5-di-tert-butyl-4-hydroxybenzylphosphonate; dioctadecyl-3,5-di-tert-butyl-4-hydroxybenzylphosphonate; dioctadecyl-5-ter-butyl-4-hydroxy-3-methylbenzylphosphonate; calcium salt of the monoethylic ester of 3,5-di-tert-butyl-4-hydroxybenzylphosphonic acid.

12. Acylamino phenols such as lauric acid 4-hydroxyanilide, stearic acid 4-hydroxyanilide, octil N-(3,5-di-tert-butyl-4-hydroxyphenyl)carbamate.

13. β-(3,5-di-tert-butyl-4-hydroxyphenyl)propionic acid esters with mono- or polyhydric alcohols such as; methanol, ethanol, n-octanol, iso-octanol, octadecanol; 1,6-esandiol, 1,9-nonadiol, ethylenic glycol, 1,2-propandiol, neopentyl glycol, thiodiethylene glycol, diethylene glycol, triethylene glycol, pentaerithrol, tri-(hydroxyethyl)isocyanurate; N,N'-bis(hydroxyethyl)oxamide; 3-thioundecanol; 3-thiopentadecanol; trimethyl hexanediol; trimethylolpropane; 4-hydroxymethyl-1-phospho-2,6,7-trioxabicyclo(2,2,2)octane.

14. β-(5-tert-butyl-4-hydroxy-3-methylphenyl)propionic acid esters with mono- or polyhydric alcohols such as; methanol, ethanol, n-octanol, iso-octanol, octadecanol; 1,6-esandiol, 1,9-nonadiol, ethylenic glycol, 1,2-propandiol, neopentyl glycol, thiodiethylene glycol, diethylene glycol, triethylene glycol, pentaerithrol, tri-(hydroxyethyl)isocyanurate; N,N'-bis(hydroxyethyl)oxamide; 3-thioundecanol; 3-thiopentadecanol; trimethyl hexanediol; trimethylolpropane; 4-hydroxymethyl-1-phospho-2,6,7-trioxabicyclo(2,2,2)octane.

15. β-(3,5-dicyclohexyl-4-hydroxyphenyl)propionic acid esters with mono- or polyhydric alcohols such as; methanol, ethanol, n-octanol, iso-octanol, octadecanol, 1,6-esandiol, 1,9-nonadiol, ethylenic glycol, 1,2-propandiol, neopentyl glycol, thiodiethylene glycol, diethylene glycol, triethylene glycol, pentaerithrol, tri-(hydroxyethyl)isocyanurate; N,N'-bis(hydroxyethyl)oxamide; 3-thioundecanol; 3-thiopentadecanol trimethyl hexanediol; trimethylopropane; 4-hydroxymethyl-1-phospho-2,6,7-trioxabicyclo(2,2,2)octane.

16. 3,5,-di-tert-butyl-4-hydroxyphenyl acetic acid esters with mono- or polyhydric alcohols such as; methanol, ethanol, n-octanol, iso-octanol, octadecanol; 1,6-esandiol, 1,9-nonadiol, ethylenic glycol, 1,2-propandiol, neopentyl glycol, thiodiethylene glycol, diethylene triethylene glycol, pentaerithrol, tri-(hydroxyethyl)isocyanurate; N,N'-bis(hydroxyethyl)oxamide, 3-thioundecanol; 3-thiopentadecanol; trimethyl hexanediol; trimethylopropane; 4-hydroxymethyl-1-phospho-2,6,7-trioxabicyclo(2,2,2)octane.

17. β-(3,5-di-tert-butyl-4-hydroxyphenyl)propionic acid amides such as: N,N'-bis(3,5-di-tert-butyl-4-hydroxyphenylpropionil)-hexamethylene diamide; N,N'-bis-(3,5-di-tert-butyl-4-hydroxyphenylpropionyl)-trimethylendiamide, N,N'-bis-(3,5-di-tert-butyl-4-hydroxyphenylpropionyl)hydrazide; N,N'-bis(2-(3-(3,5-di-tert-butyl-4-hydroxyphenyl) propionyloxy)ethyl)-oxamide.

18. Ascorbic acid (Vitamin C).

19. Amine antioxidants such as: N,N'-diisopropyl-p-phenylenediamine; N,N'-di-sec-butyl-p-phenylenediamine; N,N'-bis(1,4-dimethyl-pentyl)-p-phenylenediamine; N,N'-bis(1-ethyl-3-methylpentyl)-p-phenylenediamine; N,N'-bis (1-methylheptyl)-p-phenylenediamine; N,N'-dicyclohexyl-p-phenylenediamine; N,N'-diphenyl-p-phenylenediamine; N,N'-bis-(2-naphtyl)-p-phenylenediamine; N-isopropyl-N'-phenyl-p-phenylenediamine; N-(1,3-dimethyl-butyl)-N'-phenyl-p-phenylenediamine; N-1-methylheptyl)-N'-phenyl-phenylenediamine; N-cyclohexyl-N'-phenyl-p-phenylenediamine; 4-(p-toluensulfamoyl)-diphenylamin, N,N'-dimethyl-N,N'-di-sec-butyl-p-phenylendimine; diphenylamine; N-allyl-diphenylamine; 4-isopropoxy-diphenylamine; N-phenyl-1-naphtylamine, N-(4-ter-octylphenyl)-1-naphtylamine, N-phenyl-2-naphtylamine; p,p'-di-ter-octyldiphenylamine; 4-n-butyl-aminophenol; 4-butyryl-aminohenol; 4-nonanoylaminophenol; dodecanoyl-aminophenol; 4-octadecanoyl-aminophenol; bis(4-mothoxyhenyl)amine; 2,6-di-ter-butyl-4-dimethylaminomethylphenol; 2,4'-diaminodiphenylmethane; 4,4'-diaminodphenylmethane; N,N,N',N'-tetramethyl-4,4'-diaminodiphenylmethane; 1,2-bis-((2-methylphenyl)amino)ethane; 1,2-bis-(phenylamino) propane; o-tolil-biguanide; bis-(4-(1',3'-dimethylbutyl)phenyl)amine); ter-octy-N-phenyl-1-naphtylamine; mixtures of dialkylated tert-butyl/tert-octyl-diphenylamines; mixtures of mono- and di-alkyl nonyldiphenylamines; mixtures of mono- and di-alkyl dodecyldiphenylamines; mixtures of mono- and di-alkyl isopropyl/isohexyldiphenylamines; mixtures of mono- and di-alkyl terbutyldiphenylamines; 2,3, dihydro-3,3-dimethyl-4H-1,4-benzothiazine; phenothiazine; mixtures of mono- and di-alkyl tert-butyl/tert-octylphenothiazine; mixtures of mono- and di-alkyl tert-octyl phenothiazine; N-allyl phenothiazine; N,N,N',N'-tetraphenyl-1,4-diamino-2-butene; N,N'-bis-(2,2,6,6-tetramethyl-piperidinyl-4-hexamethylenediamine; bis(2,2,6,6-tetramethyl-piperid-4-yl)sebacate; 2,2,6,6-tetramethyl-piperid-4-one; 2,2,6,6-tetramethyl-piperid-4-ol.

B. UV Adsorbers and Light Stabilizers 1. 2-(2'-hydroxyphenyl)benzotriazoles, such as: 2-(2'-hydroxy-5-methylphenyl)benzotriazole; 2-(3',5'-di-tert-butyl-2'-hydroxyphenyl)benzotriazole; 2-(5'-tere-butyl-2'-hydroxyphenyl)benzotriazole; 2-(2'-hydroxy-5'-(1,1,3,3-tetramethylbutyl)phenil)benzotriazole; 2-(3',5'-di-tert-butyl-2'-hydroxyphenyl)-5-chloro-benzotriazole; 2-(3'-tert-butyl-2'-hydroxy-5'-methylphenyl)-5-chloro-benzotriazole; 2-(3'-sec-butyl-5'-tert-butyl-2'-hydroxyphenyl)benzotriazole; 2-(2'-hydroxy-4'-octyloxyphenyl)benzotriazole; 2-(3',5'-di-tert-amil-2'-hydroxyphenyl)-benzotriazole; 2-(3',5'-bis-(α, αdimethylbenzyl)-2'-hydroxyphenyl)benzotriazole; 2-(3'-tert-butyl-5'-(2-(2-ethylhexyloxy)-carbonylethyl)-2'-hydroxyphenyl)-5-chloro-benzotriazole; 2-(3'-tert-butyl-2'-hydroxy-5'-(2-octoxycarbonylethyl)phenil)-5-chloro-benzotriazole; 2-(3'-tert-butyl-2'-hydroxy-5'-(2-methoxycarbonylethyl)phenil)-5-chloro-benzotriazole; 2-(3-tert-butyl-2'-hydroxy-5'-(2-methoxycarbonyl-ethyl)phenil)-benzotriazole; 2-(3'-tert-butyl-2'-hydroxy-5'-(2-octyloxycarbonyl-ethyl)phenil)-benzotriazole; 2-(3'-tert-butyl-5'-(2-(2-ethylhexyloxy)-carbonylethyl)-2'-hydroxyphenyl)-benzotriazole; 2-(3'-dodecyl-2'-hydroxy-5'-methylphenyl)-benzotriazole; 2-(3'-tert-butyl-2'-hydroxy-5'-(2-isooctyloxycarbonylethyl)-phenyl-benzotriazole; 2,2'-methylene-bis-(4-(1,1,3,3-tetramethylbutyl)-6-benzotriazol-2-ylphenol); the transesterification product of 2-(3'-tert-butyl-5'-(2-methoxycarbonylethyl)-2'-hydroxyphenyl)-2H-benzotriazole with polyethylenglycole 300 (R—$CH_2$—$CH_2$—COO—$CH_2$—$CH_2$—)$_2$— wherein R can be: 3'-tert-butyl-4'-hydroxy-5'-2H-benzotriazole-2-ylphenyl; 2-(2'-hydroxy-3'-α,α-dimethylbenzyl-5'-(1,1,3,3-tetramethylbutyl)-phenyl)benzotriazole; 2-(2'-hydroxy-3'-(1,1,3,3-tetramethylbutyl)-5'-(α,α-dimethylbenzyl)phenyl) benzotriazole.

2. 2-hydroxybenzophenones such as for example the 4-hydroxy-; 4-methoxy-; octyloxy-; 4-decyloxy-; 4-dodecyloxy-; 4-benzyloxy-; 4,2',4'-tri-hydroxy- and 2'-hydroxy-4, 4'-dimethoxy derivates.

3. Esters of substituted and non-substituted benzoic acids, such as for example: 4-tertbutyl-phenyl-salicylate; phenyl salicylate; octylphenyl salicylate; dibenzoyl resorcinol; bis-(4-tert-butyl-benzoyl)-resorcinol; benzoyl resorcinol; 2,4-di-tert-butylphenyl 3,5-di-tert-buthyl-4-hydroxybenzoate; hexadecyl 3,5-di-tert-buthyl-4-hydroxybenzoate; octadecyl 3,5-di-tert-butyl-4-hydroxy-benzoate; 2-methyl-4,6-di-tert-butylphenyl 3,5-di-tert-butil-4-hydroxybenzoate:

4. Acrilates, such as for example: ethyl α-cyano-β,β-diphenylacrilate; isooctyl α-cyano-β,β-diphenylacrilate; methyl α-carbomethoxycinnamate; methyl α-cyano-β-methyl-p-methoxy-cinnamate; butil α-cyano-βmethyl-p-methyethoxy-cinnamate; methyl α-carbomethoxy-p-methoxycinnamate and N-(β-carbomethoxy-β-cyanovynyl)-2-methylindoline.

5. Nickel derivates such as for example: nickel complexes 1:1 or 1:2 with 2,2'-thio-bis-(4-(1,1,3,3-tetramethylbutyl) phenol, with or without ligands such as n-butylamine, triethanolamine or N-cyclohexyldiethanolamine; nickel dibutyldithiocarbamate; nickel salts of mono-alkyl esters (for example methyl or ethyl esters) of 4-hydroxy-3,5-di-tert-butylbenzylfosfonic acid; nickel complexes of keto-oximes, for example of 2-hydroxy-4-methylphenyl undecyl-keto-oxime; nickel complexes of 1-phenyl-4-lauroyl-5-hydroxy-pyrazole, with or without additional ligands.

6. Sterically hindered amines, such as for example: bis (2,2,6,6-tetramethyl-4-piperldinyl)sebacate CAS RN=52829-07-9; bis (2,2,6,6-tetramethyl-4-piperidinyl)succinate; bis (1,2,2,6,6-pentamethyl-4-piperidinyl)sebacate CAS RN=41556-26-7; (1,2,2,6,6-pentamethyl-4-piperidinyl)methyl sebacate CAS RN=82919-37-7; bis (1-octyloxy-2,2,6,6-tetramethyl-4-piperidinyl)sebacate CAS RN=129757-67-1; bis (1,2,2,6,6-pentamethyl-4-piperidinyl) n-butyl-3,5-di-ter-butyl-4-hydroxybenzylmalonate; the condensation product of 1-(2-hydroxyethyl)-2,2,6,6-tetramethyl-4-hydroxypiperidine with succinic acid CAS RN=65447-77-0; cyclic or linear condensates of N,N'-bis-(2,2,6,6-tetramethyl-4-piperidinyl)hexamethylenediamine with 4-tert-octylamino-2,6-dichloro-1,3,5-triazine CAS RN=7878-19-8; tris(2,2,6,6-tetramethyl-4-piperidinyl)nitrilotriacetate; tetra(2,2,6,6-tetramethyl-4-piperidinyl)-1,2, 3,4-butan-tetracarboxylate; 1,1'(1,2-ethanediyl)-bis(3,3,5,5-tetramethylpiperazinone); 4-benzoyl-2,2,6,6-tetramethylpiperidine; 4-stearyloxy-2,2,6,6-tetamethyl-piperidine CAS RN=167078-06-0; bis(1,2,2,6,6-pentamethyl-4-piperidinyl)-2-n-butyl-2-(hydroxy-3,5-di-tert-butylbenzyl)malonate CAS RN=63843-89-0; 3-n-octyl-7,7,9,9-tetramethyl-1,3,8-triazaspiro(4,5)decan-2,4-dione; bis(1-octiloxy-2,2,6,6-tetramethylpiperidinyl)sebacate; bis (1-octiloxy-2,2,6,6-tetramethyl-piperidinyl)succinate; linear or cyclic condensates of N,N'-bis-(2,2,6,6-tetramethyl-4-piperidinyl)-hexamethylenediamine with 4-morpholino-2,6-dichloro-1,3,5-triazine CAS RN=8245148-7; cyclic or linear condensates of N,N'-bis-(1,2,2,6,6-pentamethyl-4-piperidinyl)-hexamethylenediamine with 4-morpholino-2,6-dicloro-1,3,5-triazine CAS RN=193098-40-7; the condensation product of 2-chloro-4,6-bis(4-n-butylamino-2,2,6,6-tetramethylpiperidinyl)-1,3,5-triazine with 1,2-bis(3-amino-propylamino)ethane; the condensation product of 2-chloro-4,6-bis(4-n-butylamino-1,2,2,6,6-pentamethylpiperidinyl)-1,3,5-triazine with 1,2-bis(3-aminopropylamino)ethane CAS RN=106990-43-6; 8-acetyl-3-dodecyil-7,7,9,9-tetramethyl-1,3,8-triazaspiro(4,5)decan-2,4-dione; 3-dodecyl-1-(1,2,2,6,6-tetramethyl-4-piperidinyl)pyrrolidin-2,5-dione; 3-dodecyl-1-(1,2,2,6,6-pentamethyl-4-piperidinyl)pyrrolidin-2,5-dione; mixture of 4-hexadecyloxy- and 4-octadecyloxy-2,2,6,6-tetramethylpiperidine; the condensation product of N,N'-bis-(2,2,6,6-tetramethyl-4-piperidinyl)hexamethylenediamine with 4-cyclohexylamine-2,6-dichloro-1,3,5-triazine; N-(2,2,6,6-tetramethyl-4-piperidinyl)n-dodecyl succinimmide; 2-undecyl-7,7,9,9-tetramethyl-1-oxo-3,8-diazo-4-oxo-spiro(4,5)decane; the condensation product of 7,7,9,9-tetramethyl-2-cycloundecyl-1-oxo-3,8-diazo-4-oxo-spiro(4,5)decane with epichlorodrine; 1,1-bis(1,2,2,6,6-pentamethyl-4-piperidinyloxicarbonyl)-2-(4-methoxyphenyl)ethene; N,N'-bis-formil-N,N'-bis(2,2,6,6-tetramethyl-4-piperidinyl)hexemethylenediamine diester of 4-methoxy-4-methylen-malonic acid with 1,2,2,6,6-pentamethyl-4-hydroxypiperidine; poly(methylpropyl-3-oxy-4-(2,2,6,6-tetramethyl-4-piperidinyl))-siloxane; the reaction product of the copolymer maleic acid/alfa-olefins with 2,2,6,6-tetramethyl-4-aminopiperidine or 1,2,2,6,6-pentamethyl-4-amino-piperidine; condensation product of 2-chloro-4,6-bis-(4-n-butylamino-1-cyclohexyloxy-2,2,6,6-tetramethylpiperidinyl)-1,3,5-triaziny with 1,2-bis-(3-amino-propylamino)-ethane; condensation product of 1,6-hexandiamine-bis(2,2,6,6-tetramethyl-4-piperidinyl)- with the condensation product of 2,4,6-trichloro-1,3,5-triazine with di-n-butylamine and N-butyl-2,2,6,6-tetramethyl-4-piperidinamine CAS RN=192268-64-7; derivates of 7-oxa-3,20-diaza-dispiro-(5.1.11.2)-eneicosanone identified by CAS RN 64338-16-5; 85099-51-0; 85099-50-9; 202483-55-4; reaction product of 2,2,6,6-tetramethyl-4-piperidine with the polymer obtainable by copolymerization of maleic anhydride with alkenes C20-24 CAS RN=152261-33-1; products described in EP 782994.

7. Oxamides, such as for example: 4,4'-dioctyloxy-oxalanilide; 2,2'-diethoxy-oxalanilide; 2,2'-dioctiloxy-5,5'-di-ter-butyl-oxalanilide; 2,2'-didodecyloxy-5,5'-di-ter-butyl-oxalanilide; 2-ethoxy-2'-ethyloxy-oxalanilide; N,N'-bis(3-dimethylaminopropyl)oxalanilide; 2-ethoxy-2'-ethyl-5,4'-di-ter-butyl-oxalanilide; mixtures of oxalanilides o- and p-methoxy disubstituted and mixtures of oxalanilides o- and p-ethoxy disubstituted.

8. 2-(2-hydroxyphenyl)-1,3,5-triazines, such as for example: 2,4,6-tris(2-hydroxy-4-octiloxyphenyl)-1,3,5-triazine; 2-(2-hydroxy-4-octiloxyphenyl)-4,6-bis(2,4-dimethylphenyl)-1,3,5-triazine; 2,4-bis(2-hydroxy-4-propyloxyphenyl)-6-(2,4-dimethylphenyl)-1,3,5-triazine; 2-(2-hydroxy-4-octiloxyphenyl)-4,6-bis-(4-methylphenyl)-1,3,5-triazine; 2-(2-hydroxy-4-dodecyloxyphenyl)-4,6-bis-(2-4-dimethylphenyl)-1,3,5-triazine; 2-(2-hydroxy-4-tridecyloxyphenyl)-4,6-bis-(2-4-dimethylphenyl)-1,3,5-triazine; 2-(2-hydroxy-4-(2-hydroxy-3-butyloxy-propoxy)phenyl)-4,6-bis(2,4-dimethyl)-1,3,5-triazine; 2-(2-hydroxy-4-(2-hydroxy-3-octiloxy-propoxy)-phenyl)-4,6-bis(2,4-dimethyl)-1,3,5-triazine; 2-(4-(dodeculoxy/tridecyloxy-2-hydroxypropoxy)-2-hydroxyphenyl)-4,6-bis(2,4-dimethylphenyl)-1,3,5-triazine; 2-(2-hydroxy-4-(2-hydroxy-3-dodeciloxy-propoxy)phenyl)-4,6-bis(2,4-dimethylphenyl)-1,3,5-triazine; 2-(2-hydroxy-4-hexyloxy)phenyl-4,6-diphenyl-1,3,5-triazine; 2-(2-hydroxy-4-methoxyphenyl)-4,6-diphenyl-1,3,5-triazine; 2,4,6-tris(2-hydroxy-4-(3-butoxy-2-hydroxy-propoxy)phenyl-1,3,5-triazine; 2-(2-hydroxyphenyl)-4-(4-methoxyphenyl)-6-phenyl-1,3,5-triazine; 2-(2-hydroxy-4-(3-(2-ethylhexyl-1-oxy)-2-hydroxypropyloxy)phenyl)-4,6-bis(2,4-dimethylphenyl)-1,3,5-triazine.

C. Metal Deactivator

For example: N,N'-diphenyloxamide; N-salicilal-N'-bis-saliciloyl-hydrazine; N,N'-bis(saliciloyl)hydrazine, N,N'-bis(3,5-di-tert-butyl-4-hydroxyphenylpropionyl)hydrazine; 3-saliciloylamino-1,2,4-triazole; bis(benzylidene)oxalyl dihydrazide; oxalanilide; isoftaloyl dihydrazide; sebacoyl bisphenyhydrazide; N,N'-diacetyladipoyl dihydrazide; N,N'-bis(saliciloyl)oxalyl dihydrazide; N,N'-bis(saliciloyl)thiopropionyl dihydrazide.

D. Phosphites and Phosphonites

For example: triphenyl phosphite; diphenyl alchil phosphites; phenyl dialkyl phosphites; tris(nonylphenyl)phosphite; trilauryl phosphite; trioctadecyl phosphite; distearyl pentaerythritol diphosphite; tris(2,4-di-tert-butyl-phenyl) phosphite; diisodecyil pentaerythritol diphosphate; bis(2,4-di-tert-butyl phenyl) phosphite; diisodecyl pentaerythritol diphosphite; bis(2,4-di-tert-butylphenyl) pentaerythritol diphosphite; bis(2,6-di-tert-butyl-4-methylphenyl)-pentaerythritol diphosphite; diisodecyloxy-pentaerythritol diphosphite; bis-(2,4-di-tert-butyl-6-methylphenyl)pentaerythritol diphosphite; bis(2,4,6-tris(ter-butyl-6-methylphenyl)pentaerythritol diphosphite; tristearyl sorbitol triphosphite; bis(2,4-di-tert-butyl-6-methylphenyl) methyl phosphite; bis(2,4-di-tert-butyl-6-methyphenyl) ethyl phosphite; 2,2',2''-nitrilo(triethyltris(3,3',5,5'-tetra-tert-butyl-1,1'-biphenyl-2,2'-idyl) phosphite); 2-ethylhexyl (3,3',5,5'-tetra-tert-butyl-1,1'-biphenyl-2,2'-idyl) phosphite); tetra(2,4-di-tert-butylphenyl) 4-4'-biphenylene diphosphonite.

E. Hydroxylamines

For example: N,N-dibenzylhydroxyalmine; N,N-diethylhydroxylamine; N,N-dioctylhydroxylamine; N,N-dilaurylhydroxyl-amine; N,N-ditetradecylhydroxylamine; N,N-dihexadecylthydroxylamine; N,N-dioctadecylthydroxylamine; N-hexadecyl-N-octadecylhydroxylamine; N-heptadecyl-N-octadecylhydroxylamine; N,N-dialkylhydroxylamines derived from the hydrogenated tallow amines.

F. Nitrones

For examples N-benzyl-alfa-phenyl-nitrone; N-ethyl-alfa-methyl-nitrone; N-octyl-alfa-eptyl-nitrone; N-lauryl-alfa-undecyl-nitrone; N-tetradecyl-alfa-tridecyl-nitrone; N-hexadecyl-alfa-pentadecyl-nitrone; N-octadecyl-alfa-pentadecyl-nitrone; N-heptadecyl-alfa-heptadecyl-nitrone; N-octadecyl-alfa-hexadecyl-nitrone; nitrones derived from N,N-dialkylhydroxylamines obtained from amines of hydrogenated tallow.

G. Thiosynergic Derivates

For example dilauryl thiodipropionate or stearyl thiodipropionate.

H. Antiperoxide Agents

For example esters of the thiodipropionic acid with lauryl, stearyl, miristic or tridecyl alcohols; mercaptobenzimidazole or 2-mercapto-benzimidazole zinc salt; zinc dibutyldithiocarbamate; dioctadecyl disulphide; pentaerythritol tetrakis(β-dodecylmercapto)propionate.

I. Polyamide Stabilizers

For example copper salts in combination with iodides and/or phosphorated compounds and bivalent manganese salts.

L. Basic: Co-Stabilizers

For example: melamine; polyvinylpolypyrrolidone; dicyandiamide; triallylcyanurate; urea derivates; hydrazine derivates; amines; polyamides; polyurethans; alkaline metal and alkaline-earth metal salts of long-chain fatty acids such as calcium stearate, zinc stearate, magnesium behenate, magnesium stearate, sodium ricinoleate, potassium palmitate, pyrocathecol antimonium or zinc salts.

M. Nucleating Agents

For example inorganic substances such as talc; metal oxides such as titanium dioxide or magnesium oxide; phosphates, carbonates or sulphates od earth-alkaline metal salts; organic compounds such as mono or polycarboxylic acids and salts thereof such as 4-ter-butylbenzoic acid, adipic acid, diphenylacetic acid, sodium succinate; sodium benzoate; polymeric compounds such as anionic copolymers.

N. Benzofuranones and Indolinones

For example the ones described in U.S. Pat. No. 4,325,863; U.S. Pat. No. 4,338,244; U.S. Pat. No. 5,175,332; U.S. Pat. No. 5,216,052; U.S. Pat. No. 5,252,643; DE-A-4316611; DE-A-4316622; DE-A-4316876; EP-A-0589839; EP-A-0591102; 3-(4-(2-acetoethoxy)phenyl)-5,7-di-ter-butyl-benzofuran-2-one; 5,7-di-ter-butyl-3-(4-(2-stearoyloxyethoxy)phenyl)benzofuran-2-one; 3,3'-bis(5,7-di-ter-butyl-3-(4-(2-hydroxyethoxy)phenyl)benzofuran-2-one); 5,7-di-ter-butyl-3-(4-ethoxyphenyl)benzofuran-2-one; 3-(4-acetoxy-3,5-dimethylphenyl)-5,7-di-ter-butyl-benzofuran-2-one; 3-(3,5-dimethyl-4-pivaloyloxyphenyl)-5,7-di-ter-butyl-benzofuran-2-one; 3-(2,3-di-methylphenyl)-5,7-di-ter-butyl-benzofuran-2-one.

O. Fillers and Reinforcing Agents

For example: calcium carbonate; silicates; glass fibers; asbestos; talc; kaolin; mica; barium sulphate; metal oxides and hydroxides, carbon black; graphite; wood flour or fiber or other natural products; synthetic fibers.

P. Other Additives

For example plasticizers, lubricants, emulsifiers, pigments, rheology modifiers; catalysts; flow control agents; optical bleach; antiflame agents; antistatic agents, swelling agents.

The invention will be further described in greater detail with reference to the below given working examples, wherein working conditions are described that allow new polymeric polypiperidine derivatives of general formula (I), with p included between 3 and 20, to be obtained according to the present invention.

Although it is clear that general formula (I) represents the primary structure of the polypiperidine derivative, being this a polymer it may happen that different kinds of oligomeric structures are present in mixture with the primary structure (I).

Characterization of the products was directed to the determination of the molecular weight distribution (MWD) by conventional size exclusion chromatography (SEC). The technique used a differential reflectometer as concentration sensor and a relative calibration built with polystyrene (PS) standards with MWD narrow.

The samples have been solubilised in the SEC mobile phase at the desired concentration. A Waters modular chromatographic HPLC/SEC system was used.

In the sample characterization the chromatographic system has used the following experimental conditions:
Mobile phase: THF+0.08 M diethanolamine;
Columns bench: 2 Mesopore Polymer Laboratories;
Temperature: 30° C.;
Flow: 0.6 l/min;
Degassing: helium
Concentration: >>10 mg/ml;
Injection volume: 50 µL;
Test time: 40 minutes;
Calibration: polinomial relative of 3° order built with 8 polystyrene (PS) standards with MWD narrow with peak molecular weight Mp of between 95000 and 382 g/mole.

For each sample and in comparison between the sample the following parameters have been determined:
MWD;
Molecular weight average Mn, Mw;
polydispersity index: Mw/Mn.

PREPARATION EXAMPLES

Example 1

Preparation Example

A polymeric HALS having structure (I) with p=3-20, $A=(CH_2)_a$— wherein a=2, Z=formula (III) group, n=3, X and $X_1$=formula (II) group with $R_2$=butyl, R and $R_1$=H and Y=morpholine residue, has been prepared with the following described procedure.

0.24 moles of N-(2,2,6,6-tetramethyl-4-piperidinyl)-butylamine were added in 30 minutes, under stirring at room temperature, to a solution obtained by dissolving 0.12 moles of cyanuric chloride in 170 g of xilene. Then, 40 g of water and 0.27 moles of sodium hydroxide in form of 30% water solution were added and slow heating up to 93° C. was applied, this temperature was maintained for two hours, and the water phase was then removed. The obtained xilene solution, containing 0.12 moles of a compound of general formula (IX) wherein R and $R_1$=H and X and $X_1$ being both the group of formula (II) wherein $R_2$=butyl, was additioned with 0.06 moles of N,N'-bis(aminopropil)-etilendiamine, corresponding to an amine of general formula (XIII) wherein n=3 and $A=(CH_2)_a$— wherein a=2 and the acidity was neutralized with a light alkali excess. The mixture was gradually heated up to the full reflux temperature, by removing reaction water by distillation, and then maintained at the same temperature for three hours. The mixture was allowed to cool at 90° C., and 100 g of water were added; after stirring for 30' at 80-90° C. the water phase was removed.

At the xilene solution containing 0.06 moles of an amine of general formula (VII) wherein Z is the group of formula (III) and n, A, R, $R_1$, X, $X_1$ are as above defined, a mixture has been added that was obtained by dissolving 0.054 of cyanuric chloride in 100 g of xilene, under stirring and by maintaining the temperature below 30° C. Once the addition was completed, the mixture was kept under stirring for one hour and then slowly heated up to 60° C. At this temperature a slight excess (0.113 moles) of sodium hydroxide in 30% water solution was added and the mixture was slightly heated up to 90° C., at which temperature stirring was maintained for 1 h. Then, 100 g of water were added and stirring was maintained for 30' and then the water phase was removed.

0.060 moles of morpholine and a light excess of sodium hydroxide (0.070 moles) in 30% water solution were added to the so obtained xilene solution. The reaction mixture has been slowly heated, up to 110° C., temperature that has been maintained for 1 h. 100 g of water were added to the reaction mixture, once it was cooled at 90° C.; after stirring for 30 minutes at 80-90'C the water phase was removed.

Thus a xilene solution was obtained that, after filtration for removal of possible undissolved particles, was brought to dryness by distillation under vacuum of the solvent thus obtaining by cooling the melt 77.6 g of solid product (HALS 1).

Mn: 4410 g/mol (corresponding to an index p=3.30)
MW: 8539 g/mol
Polydispersity (MW/Mn): 1.94
The GPC analysis shows a chromatogram as shown in FIG. 1

Example 2

Preparation Example

A polymeric HALS having structure (I) with p=3-20, A=—(CH$_2$)$_a$— wherein a=2, Z=formula (III) group, n=3, X and X$_1$=formula (II) group with R$_2$=butyl, R and R$_1$=H and Y=group of formula (VI) wherein X and R are as defined, has been prepared with the following described procedure.

0.24 moles of N-(2,2,6,6-tetramethyl-4-piperidinyl)-butylamine were added in 30 minutes, under stirring at room temperature, to a solution obtained by dissolving 0.12 moles of cyanuric chloride in 170 g of xilene. Then, 40 g of water and 0.27 moles of sodium hydroxide in form of 30% water solution were added and slow heating up to 95° C. was applied, this temperature was maintained for two hours, and the water phase was then removed. The obtained xilene solution, containing 0.12 moles of a compound of general formula (IX) wherein R and R$_1$=H and X and X$_1$ being both the group of formula (II) wherein R$_2$=butyl, was additioned with 0.06 moles of N,N-bis(aminopropil)-etilendiamine, corresponding to an amine of general formula (XIII) wherein n=3 and A=—(CH$_2$)$_a$— wherein a=2 and the acidity was neutralized with a light alkali excess. The mixture was gradually heated up to the full reflux temperature, by removing reaction water by distillation, and then maintained at the same temperature for three hours. The mixture was allowed to cool at 90° C., and 100 g of water were added; after stirring for 30' at 80-90° C. the water phase was removed.

At the xilene solution containing 0.06 moles of an amine of general formula (VII) wherein 7 is the group of formula (III) and n, A, R, R$_1$, X, X$_1$ are as above defined, a mixture has been added that was obtained by dissolving 0.054 of cyanuric chloride in 100 g of xilene, under stirring and by maintaining the temperature below 30° C. Once the addition was completed, the mixture was kept under stirring for one hour and then slowly heated up to 60° C. At this temperature a slight excess (0.113 moles) of sodium hydroxide in 30% water solution was added and the mixture was slightly heated up to 90° C., at which temperature stirring was maintained for 1 h. Then, 100 g of water were added and stirring was maintained for 30' and then the water phase was removed.

0.054 moles of N-(2,2,6,6-tetramethyl-4-piperidinyl)-butylamine and a light excess of sodium hydroxide (0.003 moles) in 30% water solution were added to the so obtained xilene solution. The reaction mixture has been slowly heated, up to 110° C., temperature that has been maintained for 1 h. 100 g of water were added to the reaction mixture, once it was cooled at 90° C.; after stirring for 30 minutes at 80-90° C. the water phase was removed.

Thus a xilene solution was obtained that, after filtration for removal of possible undissolved particles, was brought to dryness by distillation under vacuum of the solvent, thus obtaining by cooling the melt 82.7 g of solid product (HALS 2).

Figure 2:
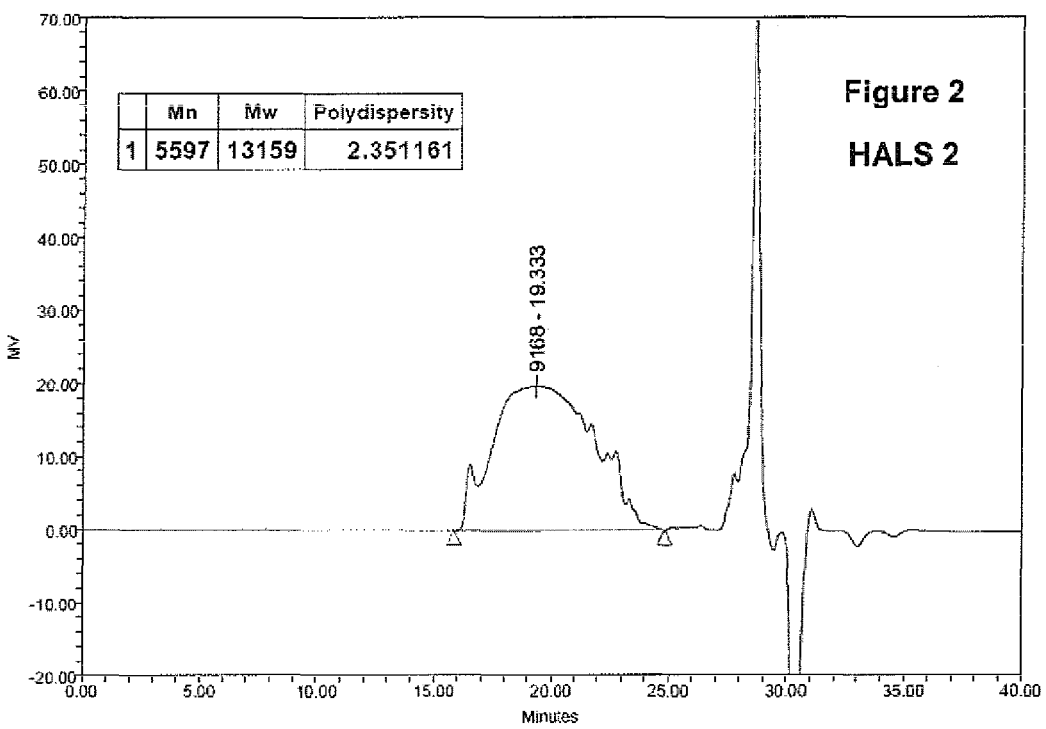
FIG. 2 shows a chromatogram referring to a high molecular weight polymeric polypiperidine compound according to the invention, obtained as described in the following example 2.

Mn: 5597 g/mol (corresponding to an index p=3.83)
MW: 13159 g/mol
Polydispersity (MW/Mn): 2.35
The GPC analysis shows a chromatogram as shown in FIG. 2.

Example 3

Comparative Preparation Example

A oligomeric HALS of structure (I) with p<3, A=—(CH$_2$)$_a$— wherein a=2, Z=formula (III) group, n=3, X and X$_1$=formula (II) group with R$_2$=butyl, R and R$_1$=H and Y=morpholine residue (HALS 3), has been prepared by adapting the procedure given in Example 1 of U.S. Pat. No. 4,477,615, using the suitable amine (XIII) with a=2 and n=3 instead of diethylenetriamine and 2,4-dichloro-6-morpholino-1,3,5-triazine instead of 2,4-dichloro-6-[(2',2',6',6'-tetramethyl-piperidin-4'-yl)-butylamino]-1,3,5-triazine.

Figure 3:
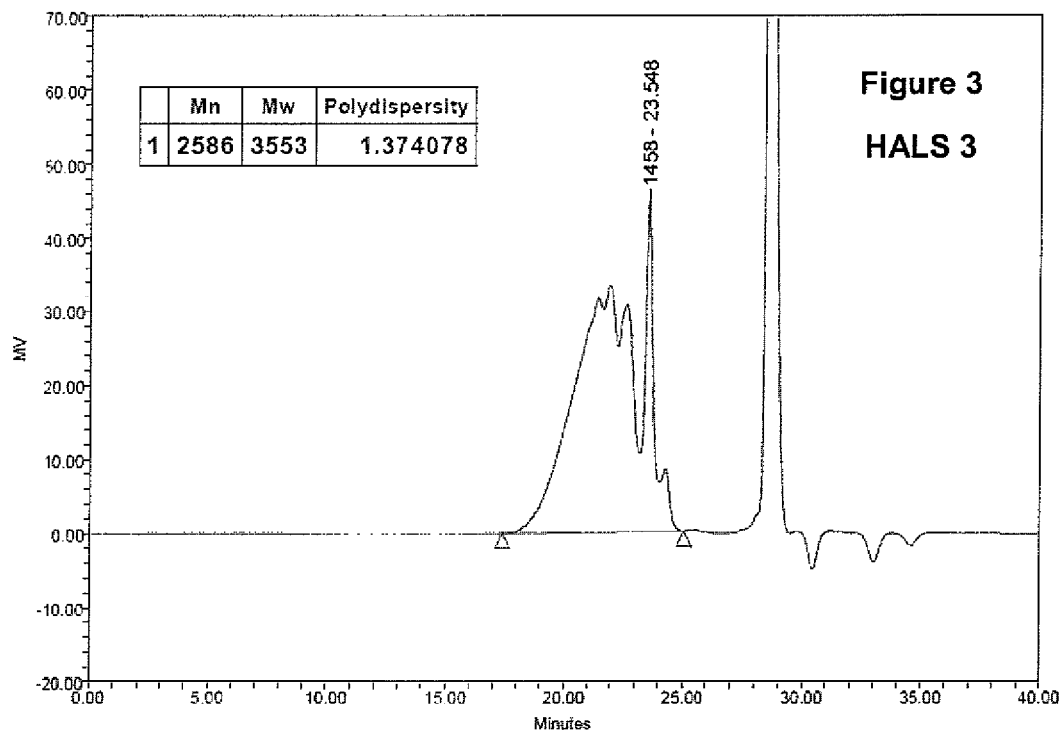
FIG. 3 shows a chromatogram referring to an oligomeric piperidine compound, obtained as described in the following comparative example 3.

Mn: 2586 g/mol (corresponding to an index p=1.94)
MW: 3553 g/mol
Polydispersity (MW/Mn): 1.37
The GPC analysis shows a chromatogram as shown in FIG. 3.

Example 4

Comparative Preparation Example

A oligomeric HALS of structure (I) with p<3, A=—(CH$_2$)$_a$— wherein a=2, Z=formula (III) group, n=3, X and X$_1$=formula (II) group with R$_2$=butyl, R and R$_1$=H and Y=group of formula (VI) wherein X and R are as defined (HALS 4), has been prepared by adapting the procedure given in Example 1 of U.S. Pat. No. 4,477,615, using the suitable amine (XIII) with a=2 and n=3 instead of diethylenetriamine.

Figure 4:
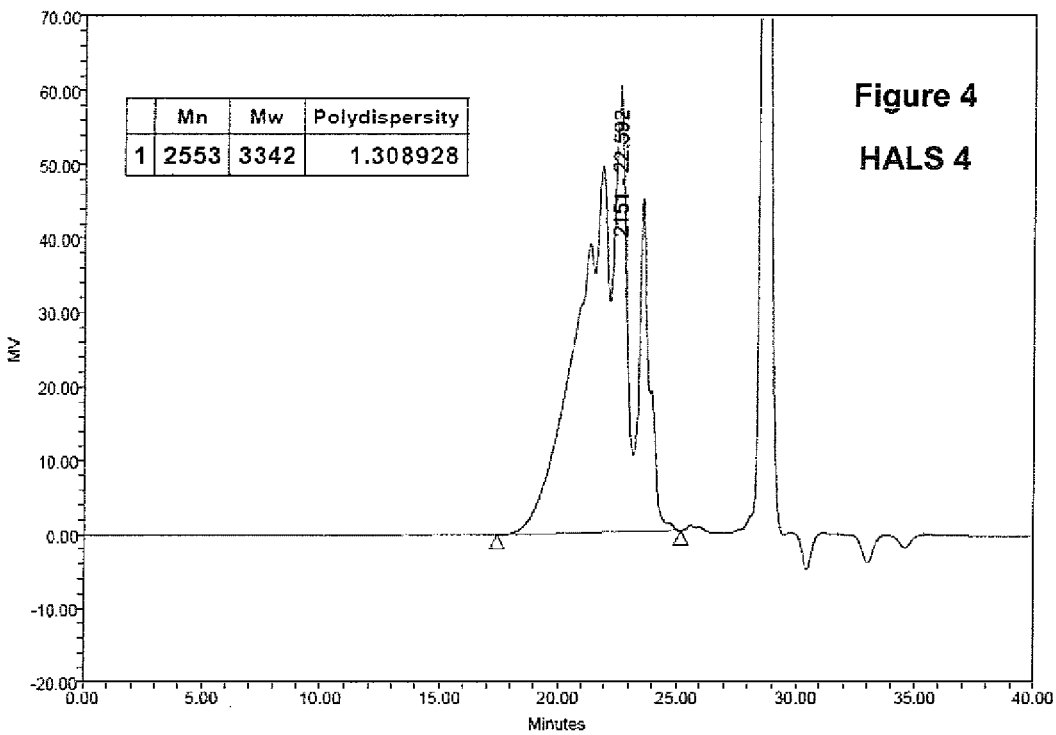
FIG. 4 shows a chromatogram referring to an oligomeric piperidine compound, obtained as described in the (allowing comparative example 4.

Mn: 2553 g/mol (corresponding to an index p=1.94)
MW: 3342 g/mol
Polydispersity (MW/Mn): 1.31
The GPC analysis shows a chromatogram as shown in FIG. 4.

In the following applicative examples, the names HALS 1, HALS 2, HALS 3 and HALS 4 indicate the compounds prepared according to the preparation examples 1, 2, 3 and 4 respectively.

The names HALS 5 and HALS 6 indicate compounds that were prepared by repeating the procedure described in preparation example 2 of US2010/0204371A1 and in preparation example 2 of U.S. Pat. No. 4,477,615, respectively.

Applicative Examples

Applicative Example 1

1000 parts by weight of powder unstabilized polypropylene homopolymer (fluidity index: about 10-12 g/10' at 230° C.-216 kP) have been mixed in a laboratory mixer with 1.0 parts by weight of calcium stearate, 0.50 parts by weight of tris-(2,4-di-tert-butyl-phenyl)phosphite, 0.50 parts by weight of 1,3,5-tris-(3,3-di-ter-butyl-4-hydroxybenzyl)isocyanurate and 1.5 parts by weight of one of the stabilizers HALS 1, 3 and 4, respectively.

The so obtained dry mixture was extruded in a laboratory extruder at 230° C. thus obtaining a granulated compound.

The granulate was then transformed into a film, having a thickness of 100 μm, by means of a compression molding laboratory press at 20° C.

Samples obtained from the different films were then exposed in Weather-Ometer Ci35A (T black panel 63±12° C., dry cycle). The samples were periodically taken and subjected to a Carbonyl index control, by means of FT-IR spectrophotometric technique. The growth of the carbonyl index value provides an indication about the degree of photo oxidative degradation of the material and may be correlated with the losing of mechanical properties following the material photooxidation.

The parameter used in order to compare the light resistance of the samples was the $t_{0.10}$ defined as the "time of WOM exposure, in hours, when a Carbonyl index value of 0.10 was reached".

The obtained experimental results are summarized in Table 1.

TABLE 1

Light stability of a PP film of 100 μm

| Stabilization | $t_{0,10}$ |
|---|---|
| Without stabilizer | 650 |
| 0.15% HALS 3 | 3200 |
| 0.15% HALS 4 | 3350 |
| 0.15% HALS 1 | 3400 |

Applicative Example 2

The dry mixture obtained as described in applicative example 1, but using in this second example 1.5 parts by weight of one of the stabilizers HALS 1, HALS 2 and HALS 4, respectively, was extruded in a laboratory extruder at 230° C. thus obtaining a granulated compound.

The granulate was then transformed into a film, having a thickness of 100 μm, by means of a compression molding laboratory press at 210° C.

Samples obtained from the different films were then exposed in Weather-Ometer Ci35A (T black panel 63±2° C., dry cycle). The samples were periodically taken and subjected to a Carbonyl index control, by means of FT-IR spectrophotometric technique. The growth of the carbonyl index value provides an indication about the degree of photo oxidative degradation of the material and may be correlated with the losing of mechanical properties following the material photooxidation.

The parameter used in order to compare the light resistance of the samples was the $t_{0.10}$ defined as the "time of WOM exposure, in hours, when a Carbonyl index value of 0.10 was reached".

The obtained experimental results are summarized in Table 2.

TABLE 2

Light stability of a PP film of 100 μm

| Stabilization | $t_{0,10}$ |
|---|---|
| Without stabilizer | 650 |
| 0.15% HALS 4 | 3350 |
| 0.15% HALS 1 | 3400 |
| 0.15% HALS 2 | 3700 |

Applicative Example 3

1000 parts by weight of unstabilized polyamide-6 were mixed in a laboratory mixer with 0.25 parts by weight of tris-(2,4-di-tert-butyl-phenyl)phosphate, 0.50 parts by weight fit 1,3,5-tris-(3,5-di-ter-butyl-4-hydoxybenzyl)isocyanurate and 5 parts by weight of one of the stabilizers HALS 1, HALS 2, HALS 5 and HAAS 6, respectively.

The dry mixture was extruded in a laboratory extruder at 260° C. and granulated after cooling the extrudate.

The granulate was then transformed, by spinning, into a bulked filament of count 270/60 (4.5 dtex/bulk), by means of a laboratory extruder at 270° C.

The filament was exposed in Weather-Ometer Ci65 (T black panel 63±2° C., dry cycle). Light resistance was monitored by periodically taking samples and subjecting to evaluation of tensile strength by checking the load at break.

The parameter used in order to compare the light resistance of the samples was the $t_{50}$ defined as the "time of WOM exposure, in hours, when a load at break of 50% of the initial value was reached".

The obtained experimental results are summarized in Table 3.

TABLE 3

| Stabilization | $t_{50}$ WOM hours |
|---|---|
| Without stabilizer | 750 |
| 0.50% HALS 1 | 3200 |
| 0.50% HALS 2 | 3080 |
| 0.50% HALS 5 | 2950 |
| 0.50% HALS 6 | 3000 |

Applicative Example 4

1000 parts by weight of unstabilized ABS (acrylonitrile-butadiene-styrene copolymer) were mixed in a laboratory mixer with 3 parts by weight of one of the stabilizers HALS 1, HALS 2, HALS 5 and HALS 6, respectively.

The dry mixture was extruded in a laboratory extruder at 250° C. and granulated after cooling the extrudate.

The granulate was then transformed into plates having 2 mm thickness, by die casting at 260° C.

The plates were exposed in Weather-Ometer Ci35A according to SAEJ1885.

Light resistance was monitored by periodically taking the plates and subjecting them to evaluation of the color.

The parameter used in order to compare the light resistance of the plates was the Yellowness index (E313), A lower value of Yellowness Index indicates a lower yellowing of the formulation exposed in WOM and therefore a better resistance of the formulation to degradation.

The obtained experimental results are summarized in Table 4.

TABLE 4

| Stabilization | Yellowing Index (E313) vs KJ/m2 at 340 nm by WOM Ci35A exposure | | | |
|---|---|---|---|---|
| | Initial | 112 KJ | 224 KJ | 448 KJ |
| Without stabilizer | 17 | 19 | 27 | 40 |
| 0.30% HALS 1 | 14 | 9.5 | 13 | 26 |
| 0.30% HALS 2 | 15 | 10.5 | 15 | 30 |
| 0.30% HALS 5 | 15.5 | 11 | 16 | 32 |
| 0.30% HALS 6 | 15.5 | 11 | 15.7 | 31 |

The invention claimed is:

1. Stabilizing polymeric polypiperidine compounds of general formula

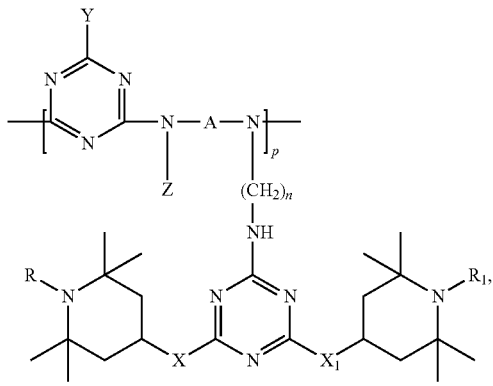

(I)

wherein p is from 3 to 6;

n is 3;

R and $R_1$, which are the same or different, are selected from the group consisting of hydrogen, linear and branched $C_1$-$C_{12}$ alkyl groups, alkenyl groups having 3 to 8 carbon atoms and aralkyl groups having 7 to 19 carbon atoms;

X and $X_1$, which are the same or different, are selected from the group consisting of oxygen and groups of formula (II)

(II)

wherein $R_2$ is selected from the group consisting of hydrogen, linear or branched $C_1$-$C_{12}$ alkyl groups, cycloalkyl groups having 5 to 12 carbon atoms and aralkyl groups having 7 to 12 carbon atoms;

A represents a —$(CH_2)_a$— group, with the proviso that a is 2;

Z is selected from the group consisting of $C_1$-$C_{18}$ alkyl groups, groups of formula (III)

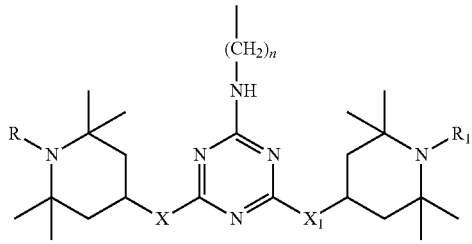

(III)

wherein n, X, $X_1$, R and $R_1$ are as above defined, and groups of formula (IV)

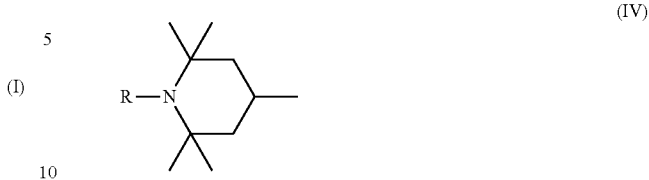

(IV)

wherein R is as above defined;

Y is a morpholine group.

2. Compounds according to claim 1 wherein R and $R_1$ are the same and represent hydrogen.

3. Compounds according to claim 1, wherein Z is a member of the group of formula (III).

4. Compounds according to claim 1, wherein X and $X_1$ are the same and correspond to the group of formula (II) with $R_2$ being n-butyl.

5. A process for the preparation of the compounds according to claim 1, comprising:

reacting cyanuric chloride and an intermediate of general formula (VII)

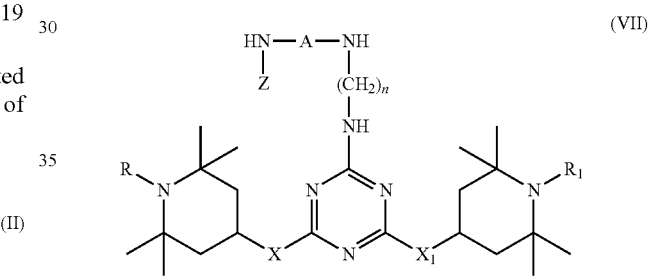

(VII)

wherein n is 3;

R and $R_1$, which are the same or different, are selected from the group consisting of hydrogen, linear and branched $C_1$-$C_{12}$ alkyl groups, alkenyl groups having 3 to 8 carbon atoms and aralkyl groups having 7 to 19 carbon atoms;

X and $X_1$, which are the same or different, are selected from the group consisting of oxygen and groups of formula (II)

(II)

wherein $R_2$ is selected from the group consisting of hydrogen, linear and branched $C_1$-$C_{12}$ alkyl groups, cycloalkyl groups having 5 to 12 carbon atoms and aralkyl groups having 7 to 12 carbon atoms, A represents a —$(CH_2)$— group, with the proviso that a is 2;

Z is selected from the group consisting of $C_1$-$C_{18}$ alkyl groups, groups of formula (III)

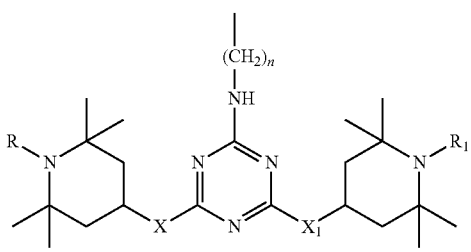

(III)

wherein n, X, X$_1$, R and R$_1$ are as above defined, and groups of formula (IV)

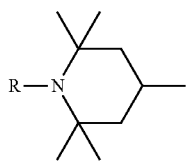

(IV)

wherein R is as above defined;
to form a compound of formula (XIV)

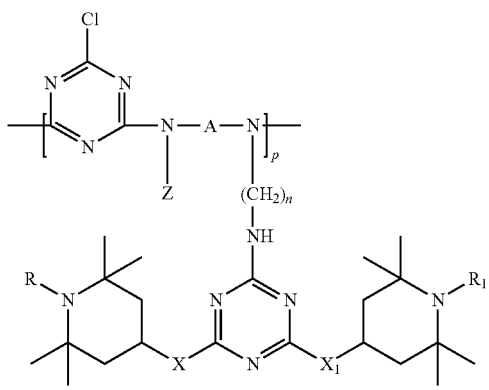

(XIV)

wherein p is from 3 to 6, Z, A, R, R$_1$, X, X$_1$ and n have the above defined meanings; and thereafter reacting the compound of formula (XIV) with morpholine.

6. A process according to claim 5, wherein said first reacting is carried out in the presence of an acidity corrector.

7. A process according to claim 6, wherein a water solution of sodium hydroxide or potassium hydroxide at a weight percent concentration of from 20% to 50% is used as acidity corrector.

8. A process according to claim 5, wherein the first reaction takes place in a range of temperature of between 5° C. and 140° C.

9. A process according to claim 8, wherein the first reacting step comprises:

adding a solution of cyanuric chloride to a solution of the compound of formula (VII);

mixing at a temperature of between 5° C. and 60° C.;

adding an acidity corrector; and progressively heating at a temperature in the range of between 80° C. and 120° C.

10. A composition comprising compounds according to claim 1 and from 0.01% to 5% by weight of a polymeric material.

11. A composition according to claim 10, wherein the polymeric material is selected from the group consisting of polyethylene, polypropylene, polystyrene, polybutadiene, polyisoprene, and copolymers thereof, polyvinylchloride, polyvnylidene chloride and copolymers thereof, polyvinylacetate and copolymers thereof, polyamides and copolymers thereof, acrylonitrile-butadiene-styrene copolymers (ABS) and polyurethanes.

12. A composition according to claim 10, wherein the polymeric material is a polyolefin.

13. A composition according to claim 10, further comprising other monomeric, polymeric or macromolecular Hindered Amine Light Stabilizer.

* * * * *